United States Patent [19]

Sternberg et al.

[11] 4,204,837
[45] May 27, 1980

[54] METHOD OF RATE IMMUNONEPHELOMETRIC ANALYSIS

[75] Inventors: James C. Sternberg, Fullerton; John E. Lillig, Diamond Bar, both of Calif.

[73] Assignee: Beckman Instruments, Inc., Fullerton, Calif.

[21] Appl. No.: 886,493

[22] Filed: Mar. 14, 1978

[51] Int. Cl.² .................... G01N 31/00; G01N 33/16; G01N 21/00
[52] U.S. Cl. ............................. 23/230 B; 356/39; 356/339; 356/341; 356/433; 424/12
[58] Field of Search ............. 356/103, 104, 39, 337, 356/338, 339, 340, 341, 433, 434; 424/12; 250/574; 23/230 B; 422/57, 58, 59

[56] References Cited

U.S. PATENT DOCUMENTS

| | | | |
|---|---|---|---|
| 3,725,204 | 4/1973 | Marshall | 356/103 |
| 3,730,842 | 5/1973 | Wyatt | 356/103 |
| 3,832,532 | 8/1974 | Praguin | 356/103 |
| 3,905,767 | 9/1975 | Morris | 23/230 B |
| 3,967,901 | 7/1976 | Rodriguez | 356/103 |
| 3,990,851 | 11/1976 | Gross | 356/103 |

Primary Examiner—Verlin R. Pendegrass
Assistant Examiner—Donald P. Walsh
Attorney, Agent, or Firm—Robert J. Steinmeyer; Robert R. Meads; John R. Shewmaker

[57] ABSTRACT

A method of determining the need for post-addition of antigen or antibody to an antigen-antibody reaction to ascertain whether the reaction is in an antigen excess or an antibody excess condition. The time rate of change of a nephelometric signal developed from the reaction is monitored to generate a rate signal having a peak value providing a measure of antigen concentration. The post-addition step is performed only if the peak rate value is ambiguous—, i.e. if it indicates one antigen concentration value for a reaction in antigen excess but another value for a reaction in antibody excess. The need for the post-addition step is determined from measured qualities of the rate signal including one or more of (1) the peak rate value, (2) the elapsed time from the start of the reaction to the peak rate, and (3) the product of the peak rate and the elapsed time. When required, the post-addition step may be performed during progress of the antigen-antibody reaction after measurement of the peak rate value.

19 Claims, 5 Drawing Figures

METHOD OF RATE IMMUNONEPHELOMETRIC ANALYSIS

CROSS-REFERENCE TO RELATED APPLICATION

This application is related to U.S. Application Ser. No. 796,621 (Anderson et al.) filed May 16, 1977, entitled A SYSTEM FOR RATE IMMUNONEPHELOMETRIC ANALYSIS, now U.S. Pat. No. 4,157,871, which is a continuation-in-part of U.S. Application Ser. No. 692,089 filed June 2, 1976, now abandoned.

BACKGROUND OF THE INVENTION

1. Field of the Invention

The present invention relates to rate immunonephelometric techniques of analyzing precipitate-forming antigen-antibody reactions and, more particularly, to methods of determining the antigen excess or antibody excess condition of such reactions.

2. Description of the Prior Art

The aforementioned Anderson et al. application discloses a system for the nephelometric assay of antigens and antibodies. For this purpose, an antigen-antibody precipitate forming reaction is conducted in an optically transparent sample container or vial. An excitation system directs a beam of light into the sample container and a detection system measures light scattered at a forward angle by the precipitate. The detected nephelometric or light scatter signal is differentiated to derive a rate signal the peak value of which provides a measure of the concentration of the desired antigen or antibody reaction component.

In immunonephelometric analysis, antigen-antibody reactions are conducted to determine the concentration of sample antigen or the concentration of sample antibody. For antigen determination, the reaction is conducted using antibody as reagent for sample antigen. Conversely, for antibody determination, the reaction is conducted using antigen as reagent for sample antibody. For ease of presentation, the present specification treats only the determination of antigen concentration. However, it should be understood that terms "antigen" and "antibody" in the present specification and claims can be interchanged throughout to describe the determination of antibody concentration.

In the Anderson et al. application, it is pointed out that the peak value of the rate signal is double-valued in that a single peak value corresponds to two widely different antigen concentration values. On a plot of peak rate vs. antigen concentration, the peak rate increases from zero to a maximum and then decreases from the maximum with further increases in antigen concentration. On the ascending limb of the curve, at lower antigen concentrations, the reaction is in an antibody excess condition. On the descending limb, at higher antigen concentrations, the reaction is in antigen excess.

The measuring range of the nephelometer for measuring antigen concentrations is preferably on the ascending limb of the curve in the antibody excess region. Consequently, if it is determined that a measured peak rate value in fact corresponds to a higher antigen concentration on the descending limb in antigen excess, it is necessary to dilute and remeasure the sample one or more times until a peak rate measurement in antibody excess is obtained. Once an acceptable peak rate measurement in antibody excess is derived from the diluted sample, the corresponding antigen concentration value is scaled upward by the prior dilution factor to determine the actual antigen concentration of the original sample. Consequently, before a peak rate measurement can be accepted, it must be determined whether the reaction for which such peak rate was measured proceeded in antigen excess (requiring sample dilution and remeasurement) or in antibody excess (acceptable).

Several papers have appeared which deal with the nephelometric assay of antigen-antibody reactions and which address the problems in determining the antigen or antibody excess condition of such reactions. These references include: (1) Savory, J., Buffone, G. J., and Reich, R., Kinetics of the IgG-anti-IgG reaction as evaluated by conventional and stopped-flow nephelometry. *Clin. Chem.* 20, 1071 (1974); (2) Buffone, G. J., Savory, J., and Cross, R. E., Use of a laser-equipped centrifugal analyzer for kinetic measurement of serum IgG. *Clin. Chem.* 20, 1320 (1974); (3) Buffone, G. J., Savory, J., Cross, R. E., and Hammond, J. E., Evaluation of kinetic light scattering as an approach to the measurement of specific proteins with the centrifugal analyzer. I. Methodology. *Clin. Chem.* 21, 1731 (1975); (4) Buffone, G. J., Savory, J., and Hermans, J., Evaluation of kinetic light scattering as an approach to the measurement of specific proteins with the centrifugal analyzer. II. Theoretical considerations. *Clin. Chem.* 21, 1735 (1975); and (5) Tiffany, T. O., Parella, J. M., Johnson, W. F., and Burtis, C. A., Specific protein analysis by light-scatter measurement with a miniature centrifugal fast analyzer. *Clin. Chem.* 20, 1055 (1974).

In references (1) and (2) the authors discuss a two-point, semi-kinetic method for measuring specific proteins by deriving the average rate of change of scatter between two fixed times. They recognize that scatter intensity rises more rapidly, in comparison with the end value it approaches, in antigen excess than in antibody excess. However, no method is suggested for utilizing such behavior for making an antigen or antibody excess determination. In fact, several of the same authors in subsequently published references (3) and (4) state "Consideration of later time intervals with the use of both PBS and PEG-PBS have not demonstrated any unique kinetic characteristics on which differentiation of either antigen or antibody excess samples could be based" (reference 3), and "Though probably more easily performed than the equilibrium method, the kinetic procedure cannot directly detect antigen excess at the present time" (reference 4). Consequently, while these authors recognize several fundamental properties of antigen-antibody reactions, they do not teach any kinetic methods for making antigen or antibody excess determinations.

The authors of reference (5) studied both the kinetic and the equilibrium measurement of antigen-antibody reactions and found better precision with equilibrium measurements. Again, as in references (1)–(4), no kinetic methods are disclosed in reference (5) for making antigen or antibody excess determinations. However, the authors do disclose a method of determining antigen excess for equilibrium measurements by measuring a change in equilibrium light scatter intensity caused by the post-addition of a small quantity of antibody into the reaction cell after the primary antigen-antibody reaction has reached equilibrium. If the primary reaction proceeded in an antigen excess condition, and additional antibody is injected into the reaction cell containing the equilibrated reaction components, the excess antigen reacts with the injected antibody and produces a significant change in scatter intensity. On the other hand, if the primary reaction proceeded in antibody excess, subsequent injection of the additional antibody produces an insignificant response. Consequently, the uniquely different responses upon post-addition of antibody provide an indication of the antigen or antibody excess condition of the primary reaction.

Unfortunately, while determination of antigen or antibody excess by the post-addition of reactant into the primary reaction is a reliable technique, it is time consuming to perform. In this regard, reference (5) employs the post-addition step only with equilibrium measurements. Consequently, a time delay is introduced while waiting for the primary reaction to reach equilibrium before the post-addition step. Post-addition delays are even more critical in nephelometers which analyze samples one at a time, as opposed to the simultaneous analysis in the centrifugal analyzer of reference (5), particularly where post-addition is performed on every sample. It should be noted that reference (5) is silent on any technique for determining antigen excess in kinetic measurements, whether by post-addition or by analysis of the kinetic data itself.

The aforementioned Anderson et al. application, on the other hand, sets forth several kinetic methods for determining antigen excess. In one method, the peak rate value and the elapsed time from the start of a reaction to occurrence of the peak rate are graphed as a function of increasing antigen concentration for a fixed antibody concentration. By an appropriate coordinate transformation technique described in the application, a plot is derived which establishes a single valued function, derived from the peak rate and the time thereto, distinguishing antigen excess from antibody excess. In a second method, the rate signal (which is the first derivative of the nephelometric signal) is differentiated to generate the second derivative of the nephelometric signal. The elapsed time from the start of the reaction to the occurrence of the peak of the rate signal is determined together with the time difference between the peak value of the rate signal and the peak value of the second derivative signal. A ratio is established of the elapsed time to the peak rate divided by the time difference between the peak values of the first and second derivative signals, and this ratio was found to distinguish antigen excess from antibody excess.

Both of the above mentioned Anderson et al. methods have the advantage of providing information during the normal course of a rate nephelometric analysis as to whether a sample is in antigen or antibody excess. While exhibiting such advantage, the methods appear to possess several drawbacks which reduce their current desirability for use in commercial instrumentation. For example, the working range for which the methods are optimized is somewhat restricted if one considers the various antigens and antibodies which a commercial instrument should measure. Moreover, the methods appear to be sensitive to noise and artifacts associated with injection transients.

In view of the foregoing, it would be desirable to derive a method for determining antigen or antibody excess in a kinetic environment which retains the reliability of the post-addition method but which minimizes the time delays heretofore associated therewith. The present invention fulfills these needs.

SUMMARY OF THE INVENTION

The present invention resides in a method of nephelometric analysis of antigen-antibody reactions employing kinetic procedures to determine whether the reaction is an antigen excess or antibody excess condition. To this end, a first reaction is initiated between antigen and antibody reaction components and the rate of change with respect to time of a nephelometric signal derived from said reaction is monitored to develop a rate signal, the peak value of which provides a measure of antigen concentration. It has been discovered that the rate signal provides kinetic information for many samples from which the antigen or antibody excess condition of the first reaction can be determined without the need for a further step of post-addition of antigen or antibody to the reaction.

In this regard, the peak value alone can provide the basis for eliminating the post-addition test for antigen or antibody excess. To this end, a normal measuring range of peak values between upper and lower thresholds is established which defines an ambiguous zone for peak values for which a sample may be in either antigen or antibody excess. Samples providing peak heights greater than the upper threshold can immediately be eliminated for being greater than the normal measuring range, i.e. rejected as clearly in antigen excess, or as in near-equivalence whether on the antibody or antigen excess side of the kinetic equivalence point. Samples having a peak height lower than the lower threshold can be regarded as clearly on the antibody excess portion of the response curve since it has been found unlikely that antigen excess samples in a physiologically feasible range will exhibit peak heights less than the lower threshold. Consequently, samples exhibiting peak height values below the lower threshold do not require that a post-addition step be performed to determine the antigen or antibody excess condition. Similarly, samples exhibiting peak height values above the upper threshold, while not acceptable, do not require a post-addition step to determine the antigen or antibody excess condition. Such sample measurements are immediately rejected without post-addition, and the reaction is repeated at a higher dilution (lower concentration) of antigen. The post-addition step for determining the antigen or antibody excess condition is therefore necessary only for samples having peak height values within the ambiguous zone.

For certain samples, it has been found that the lower threshold must be set so low that it would be necessary to perform a post-addition step on almost every sample below the upper threshold. For such samples, further criteria have been developed for determining the need for the post-addition step including: (1) the elapsed time from the start of the reaction to the peak rate and (2) the product of the elapsed time and the peak rate. A first threshold is established for the product of the peak rate and the elapsed time thereto above which an ambiguity is indicated in the antigen measurement. A second threshold is established for the elapsed time above which an ambiguity is indicated in the antigen measurement even if the product is less than the first mentioned threshold. Such ambiguous measurements necessitate the post-addition step. Further, measurements below a given peak height threshold also necessitate post-addition. Once again, measurements above an upper peak height threshold are immediately rejected without performing the post-addition step, and the reaction is repeated at a higher dilution (lower concentration) of antigen.

By means of the present invention, it has been possible to eliminate the post-addition step for antigen excess determination in as many as seventy to ninety percent of samples in a typical run thereby saving operator time and increasing the throughout of the associated nephelometer. Since the foregoing methods evaluate kinetic information of the reaction, they can determine the need for post-addition while the first reaction is in progress and the post-addition step, if necessary, can be executed at any point during the reaction after measurement of the peak rate value. Thus, by virtue of the methods of the invention, the need for the post-addition step is rapidly determined by kinetic methods which eliminate the step for many samples but enable it to be performed rapidly, when necessary, while the reaction is still in progress before reaching equilibrium.

DESCRIPTION OF THE PREFERRED EMBODIMENTS

Figure 1:
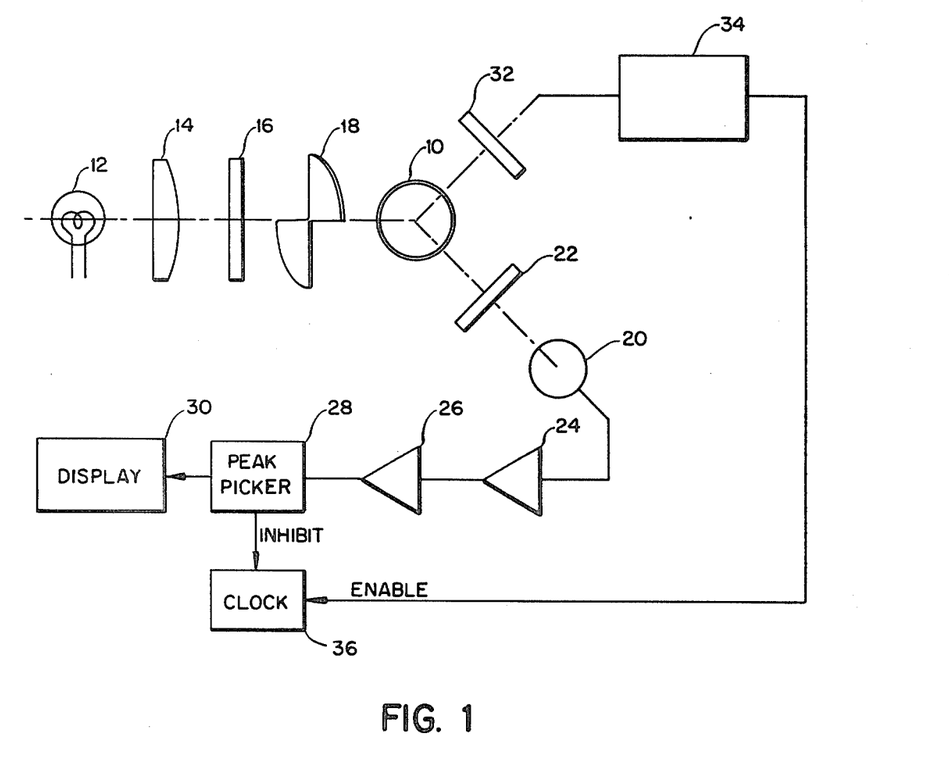
FIG. 1 is a combined block diagram and electrical schematic of a nephelometer for practicing the method of the present invention.

FIG. 1 illustrates one suitable nephelometer which may be employed to practice the methods of the present invention. The nephelometer of FIG. 1 is essentially that disclosed in the aforementioned copending Anderson et al. application and is manufactured by the assignee of the present invention. The nephelometer comprises a sample container 10, preferably a cylindrical glass vial, into which the antigen and antibody reaction components are introduced. Excitation light is directed toward and into the sample container from a light source 12, such as an incandescent lamp, through a lens system 14 and a primary filter 16, which establishes an excitation wavelength band. Prior to entering the sample container, the excitation energy is chopped or modulated by a rotating optical chopper 18 in a conventional manner. Light scattered from the precipitate produced by the antigen-antibody reaction exits the container at a forward angle and is directed toward an optical detector 20, such as a photomultiplier tube, through a secondary filter 22 for isolating the wavelength band to be measured.

The nephelometric signal generated by detector 20 in response to light scattered from the precipitate is passed through a synchronous amplifier 24 synchronized with chopper 28. The amplified nephelometer signal is then differentiated by rate amplifier 26 to generate a rate signal indicative of the time rate of change of the nephelometric signal. A peak picker 28 monitors the rate signal for its peak rate value and retains the peak value for display by display 30, and the peak rate provides a measure of the concentration of the antigen or antibody component of interest.

The nephelometer of FIG. 1 further includes apparatus for determining the elapsed time between the start of the antigen-antibody reaction in sample container 10 and the occurrence of the peak rate value of the rate signal. To this end, and as disclosed in detail in further copending U.S. Application Ser. No. 692,159 (Anderson), filed June 2, 1976, entitled METHOD AND APPARATUS FOR SIGNALLING THE INTRODUCTION OF CHEMICAL REACTION COMPONENTS INTO A CHEMICAL ANALYZING SYSTEM now U.S. Pat. No. 4,101,276, a triggering fluorescent dye is included in the last reaction component introduced into the sample container 10. The triggering dye fluoresces upon absorbing energy from the primary beam from light source 12, and such fluorescence is detected to signal the start of the reaction. For this purpose a long pass filter 32 isolates the fluorescent emission of the triggering dye and passes it to a suitable trigger circuit 34. The trigger circuit includes a light sensitive diode and an associated pulse generator which generates a trigger pulse in response to the fluorescent emission at the start of the reaction. The trigger pulse is coupled as a triggering input to start a timing clock 36. The clock also receives an inhibiting input from peak picker 28 which stops the clock upon the detection of the peak value of the rate signal. Consequently, clock 36 is enabled at the start of the antigen-antibody reaction and is inhibited when the peak rate is detected and thereby provides a measure of the elapsed time between the start of the reaction and the occurrence of the peak rate.

Figure 2:
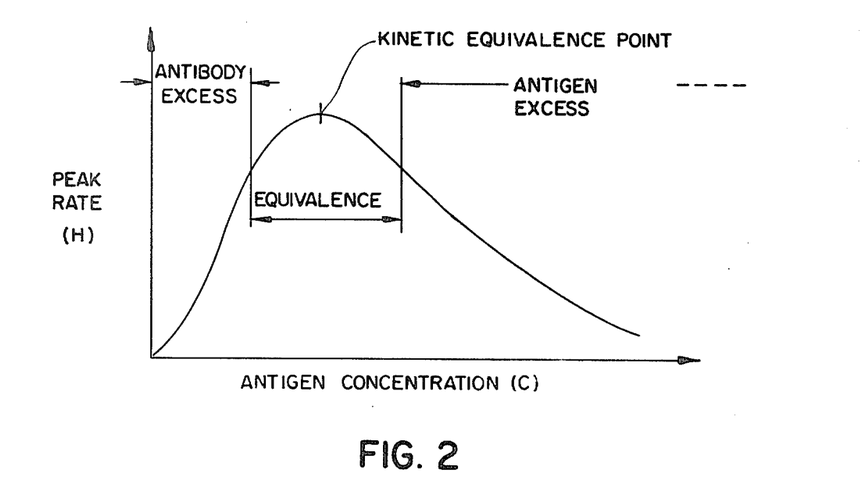
FIG. 2 is a graphical plot of peak rate of change of a nephelometric signal vs. antigen concentration plotted for a predetermined antibody concentration and illustrates regions of antibody excess, antigen excess, and near-equivalence.

FIG. 2 illustrates a plot of peak values of the rate signal (ordinate) vs. antigen concentration (abscissa) for a fixed antibody concentration. The curve is divided into three general areas labeled antibody excess, near-equivalence, and antigen excess. The ascending limb of the curve defines the antibody excess region, while the descending limb defines the antigen excess region. Between the two on either side of the kinetic equivalence pointed at maximum peak rate value is the region termed near-equivalence in which neither antigen nor antibody is present in great excess and in which a small change in peak rate represents a relatively large change in antigen concentration. As noted previously, the measuring range of the nephelometer is in the antibody excess region of the curve, and hence it is necessary that all measured samples fall into the antibody excess portion. The problem posed by the plot of FIG. 2 is that peak rate values are double valued—that is, a single peak rate value may represent two widely differing antigen concentration values depending upon the antigen or antibody excess condition of the reaction.

In accordance with a primary aspect of the present invention, the peak value of the rate signal has been discovered to have qualities which can accurately indicate the antigen or antibody excess condition of the reaction for many samples. In one embodiment of the invention the peak rate signal is measured and compared to predetermined criteria in order to determine if the peak rate is a valid measurement, to determine if the reaction should be repeated at a different antigen dilution, and to determine whether it is necessary or not to perform a postaddition step to ascertain the excess condition of the reaction. In another embodiment, further measured criteria include the elapsed time from the start of the reaction to the peak rate value in conjunction with the product of the peak rate and the elapsed time.

Figure 3:
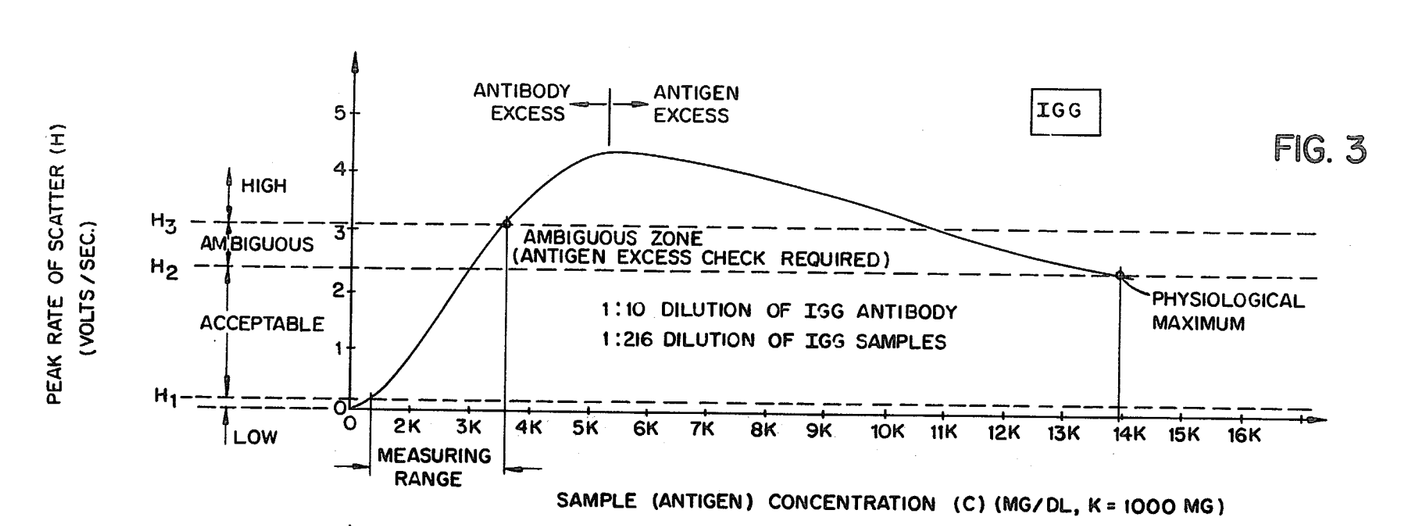
FIG. 3 is a graphical plot of peak rate vs. antigen concentration for sample IgG and illustrates peak rate threshold values defining ranges of peak rates for determining the antigen or antibody excess from the peak rate signal.

The method of analysis of the present invention will be described as applied to the measurement of immunoglobulin G (IgG) and to immunoglobulin M (IgM). Turning first to IgG, FIG. 3 illustrates a plot of peak rate vs. sample antigen concentration developed using the nephelometer of FIG. 1. The peak rate axis (Y-axis) is labeled in H units where H=relative rate units R.U. (volts/sec.). The antigen axis (X-axis) is labeled in milligrams/deciliter (mg/dl) from 0 to about 14 k where k=1000 mg/dl. The plot depicts the change in peak rate for increasing sample antigen concentration at a fixed antibody concentration. The plot was developed using anti-human IgG antiserum obtained from goats; calibration values are traceable to a World Health Organization standard. The IgG antiserum was a nephelometric grade material obtained from Atlantic Antibodies, Inc., Scarborough, Maine. The IgG antiserum was diluted in the ratio 1:10 with a 50 mM phosphate buffered saline solution. The IgG-containing serum samples were diluted in the ratio 1:216 with an isotonic saline solution. 42 $\mu$l of diluted reference serum were introduced into 600 $\mu$l of 50 mM phosphate buffered saline containing 4.4% polyethylene glycol. Within 20 seconds, 42 $\mu$l of the diluted antiserum was then introduced into the stirred reaction mixture, and the nephelometric response was monitored as a function of time.

In practicing the method of the present invention, the FIG. 3 plot of peak rate vs. antigen concentration is divided into a plurality of segments between peak rate threshold values $H_1$, $H_2$, and $H_3$.

The first segment extends from zero to threshold value $H_1$ on the ascending limb of the curve. Peak rate responses on this segment are considered to be in a low zone and are designated out of range low. Because of their low level, such responses are difficult to discriminate from background noise. Consequently, if a peak rate is measured below signal-to-noise threshold $H_1$, the reaction is simply repeated at a lower dilution (higher concentration) of antigen.

The segments on the ascending limb of the curve between peak values $H_1$ and $H_2$ and between peak values $H_2$ and $H_3$ together define the measuring range of the FIG. 1 nephelometer. That is, to be acceptable the measurement of each sample antigen must generate a peak value falling within the nephelometer measuring range.

It has been found that there is a physiological maximum value of antigen concentration which will be encountered in the measurement of serum IgG. That is, it is extremely unlikely that any sample measurements would result in a higher IgG concentration value than the labeled "physiological maximum" on the descending limb of the FIG. 3 curve. In accordance with the present invention, the peak rate threshold $H_2$ is established at a value corresponding to the physiological maximum antigen concentration. As a result, any measured values of peak rate less than $H_2$ lie unambiguously on the antibody excess side of the curve since such peak rates would correspond to sample concentrations in antigen excess beyond the physiological maximum. Consequently, samples producing peak rate values less than threshold $H_2$ (and above signal-to-noise threshold $H_1$) can be immediately accepted as a valid measurement for which it is unnecessary to perform a post-addition test for antigen or antibody excess determination.

It has further been found undesirable to use peak rate responses above threshold $H_3$ even if on the antibody excess side of the curve. As the peak rate increases above $H_3$, a small variation in peak rate corresponds to a large variation in antigen concentration and hence can lead to relatively large concentration errors in this region. As a result, peak rate threshold $H_3$ is established to define the upper limit of the nephelometer measuring range for acceptable peak rate measurements. Consequently, a sample generating a peak rate in excess of threshold $H_3$ is immediately rejected as out of range high as either in antigen excess or near-equivalence. The post-addition step to determine the excess condition is not required, and instead the reaction is repeated at a higher dilution (lower concentration) of antigen. It is unnecessary to determine whether such reactions are precisely in antigen excess or in antibody excess since the results are rejected in either case. Consequently, for purposes of description such reactions are regarded as being either in antigen excess or in near-equivalence whether on the antigen excess or antibody excess side of the curve.

In accordance with a further aspect of the invention, the peak rate thresholds $H_2$ and $H_3$ define therebetween an ambiguous after introduction of the last reaction component (herein IgG antiserum) zone for peak rate values within which it is necessary to decide whether a given peak rate lies on the antibody excess or antigen excess side of the curve. Consequently, only reactions producing peak rates between thresholds $H_2$ and $H_3$ require a post-addition step to determine the antigen or antibody excess condition of the reaction.

For the IgG reaction, the peak value of the rate signal is typically measured and displayed within a range of 20–40 seconds and can be immediately compared with the ranges established by thresholds $H_1$, $H_2$, and $H_3$, to determine if the peak value falls within the ambiguous zone between $H_2$ and $H_3$. In this manner, the need for post-addition is determined rapidly during the first reaction and the post-addition step may be performed even before the first reaction reaches equilibrium.

When an ambiguous peak rate value is measured between threshold levels $H_2$ and $H_3$, the post-addition step is performed by adding a quantity of antigen (or antibody) to the first reaction in container 10 (FIG. 1). Detector 20 responds to any change in light scatter caused by precipitate formation after the post-addition. In this regard, and assuming IgG antigen is added, if the first reaction was in antibody excess, the added antigen reacts therewith to produce additional precipitate and hence a significant change in measured light scatter. On the other hand, if the first reaction was in antigen excess, addition of further antigen produces little or no further precipitate and hence an insignificant change in light scatter. Consequently, this uniquely different behavior upon post-addition of antigen provides an indication of the antigen or antibody excess condition of the first reaction.

Using the foregoing criteria, it has been found that the post-addition step is unnecessary for as many as ninety percent of a typical population of IgG samples.

In accordance with a further aspect of the invention, the post-addition nephelometric signal generated by detector 20 is also differentiated by rate amplifier 26 and the peak value $H_{PA}$ of this second (or post-addition) rate signal is held by peak picker 28. FIG. 5 illustrates (1) a typical peak rate vs. original antigen concentration waveform similar to FIGS. 3-4 and (2) a corresponding post-addition peak rate $H_{PA}$ vs. the same original antigen concentration waveform. Note that $H_{PA}$ decreases steadily from a maximum value in antibody excess to a minimum in antigen excess. Post-addition peak rate $H_{PA1}$ corresponds to the highest acceptable antigen concentration value in the ambiguous zone between peak rate values $H_2$ and $H_3$ in antibody excess. Post-addition peak rate value $H_{PA2}$ corresponds to the lowest antigen concentration value in the ambiguous zone between peak rate values $H_2$ and $H_3$ in antigen excess. Thus, a post-addition peak rate value exceeding $H_{PA1}$ indicates that the first reaction was in antibody excess. Conversely, a post-addition peak rate value less than $H_{PA2}$ indicates that the first reaction proceeded in antigen excess. In practice, it is only necessary to establish a single post-addition peak rate threshold ($H_{PAT}$) intermediate $H_{PA1}$ and $H_{PA2}$ in order to distinguish antibody excess from antigen excess. Thus, antigen or antibody excess is determined, when required, rapidly by a single measurement comparing $H_{PA}$ to a threshold ($H_{PAT}$) value between $H_{PA1}$ and $H_{PA2}$. In this regard, a measured post-addition peak rate value greater than $H_{PAT}$ indicates an antibody excess condition for the first reaction, while a value less than $H_{PAT}$ indicates an antigen excess condition. If antigen excess is determined, the reaction is repeated at a higher antigen dilution. If antibody excess is determined, the peak rate value in antibody excess is accepted as valid.

The post-addition step may be performed at any time after measurement of the peak rate of the first reaction without waiting for the reaction to reach completion. In some cases it may be desired to perform the post-addition at or after a predetermined point is reached for each reaction, e.g. at or after the level of the rate signal decays to a predetermined value. Thus, when the measuring and comparing steps indicate an ambiguity requiring post-addition, a signal may be displayed to an operator by display 30 indicating that post-addition is required and a further indication may be displayed signalling the time when the post-addition should be performed. The latter may be achieved by signalling when the rate signal of the first reaction decays to a predetermined threshold value after passing through its peak value H.

Figure 4:
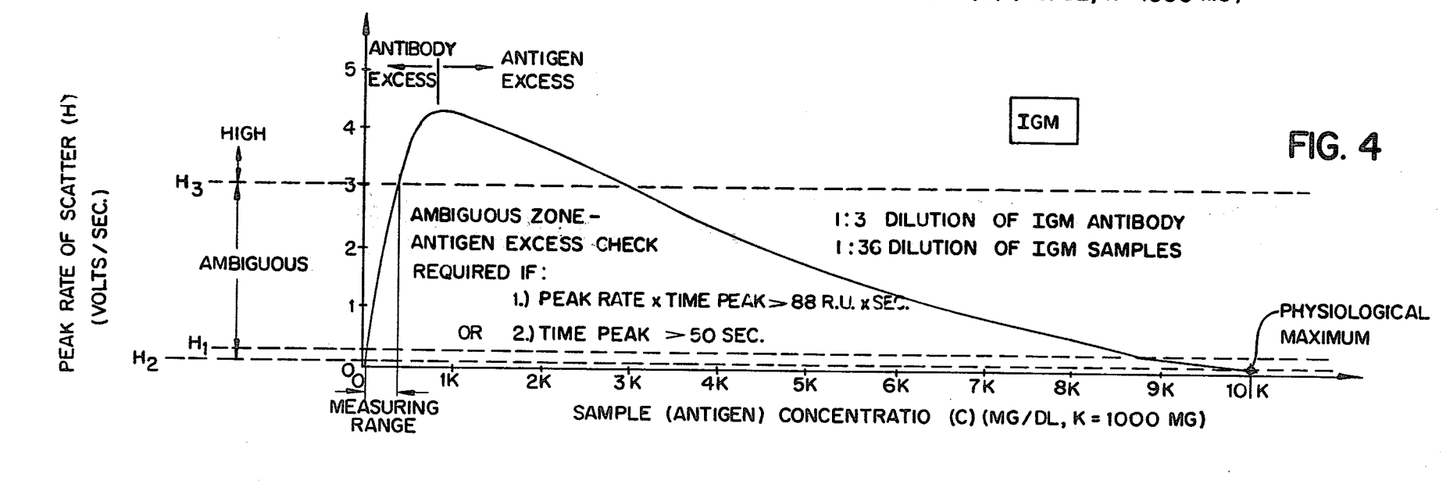
FIG. 4 is a graphical plot, similar to FIG. 3, of peak rate vs. antigen concentration for sample IgM.
Figure 5:
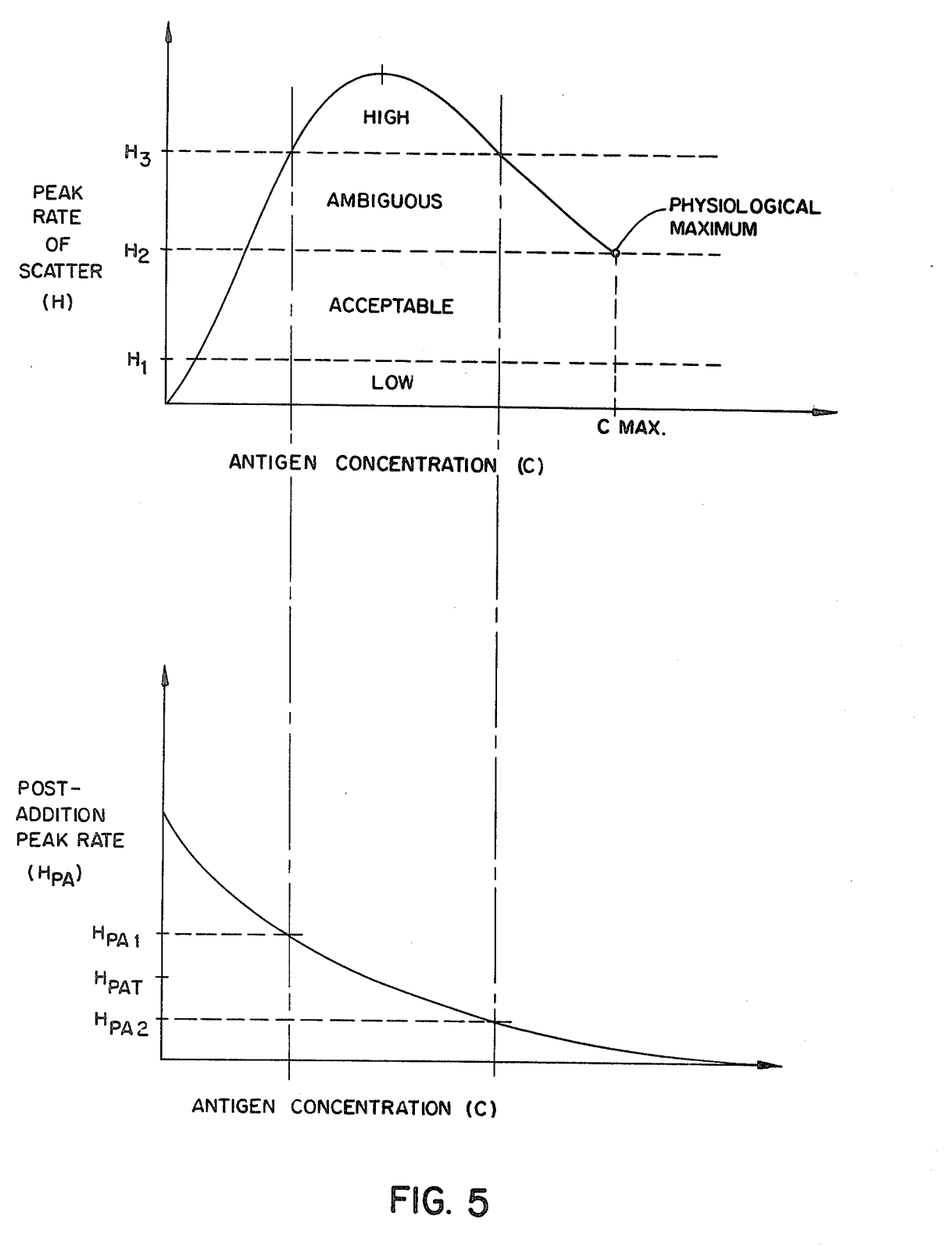
FIG. 5 is a combined graphical plot of post-addition peak rate vs. original antigen concentration and peak rate vs. original antigen concentration.

FIG. 4 illustrates the peak rate of scatter vs. antigen concentration for the more complex case of immunoglobulin M (IgM). FIG. 4 is labeled identically to FIG. 3. The plot was developed with anti-human IgM antiserum obtained from goats; calibration values are traceable to a World Health Organization standard. The IgM antiserum was a nephelometric grade material obtained from Atlantic Antibodies, Inc., Scarborough, Maine. The IgM antiserum was diluted in the ratio 1:3 with 50 mM phosphate buffered saline solution. The IgM-containing serum samples were diluted by the ratio 1:36 with isotonic saline solution. 42 $\mu$l of diluted serum was introduced into 600 $\mu$l of 50 mM phosphate buffered saline containing 4.4% polyethylene glycol. Within 20 seconds, 42 $\mu$l of the diluted antiserum was then introduced into the stirred reaction mixture, and the nephelometric response was monitored as a function of time.

It was found with IgM that the physiological maximum of antigen concentration occurs at a very low peak rate value. Thus, establishing peak rate threshold $H_2$ at the "physiological maximum" produces a much wider ambiguous zone between threshold values $H_2$ and $H_3$ for which the post-addition test would be required. In fact, in FIG. 4 threshold $H_2$ is less than threshold $H_1$. It is apparent that with such an expanded ambiguous zone, the post-addition step would be required for virtually every sample generating a peak rate less than threshold $H_3$.

In accordance with a further aspect of the invention, other criteria were developed to circumvent the foregoing problem and reduce the number of IgM samples requiring a post-addition test. To this end, the criteria developed include: (1) the elapsed time between the start of the first reaction and the occurrence of the peak rate value and (2) the product of the elapsed time and the peak rate. The elapsed time is expressed in seconds and the peak rate in relative rate units R.U. (volts/sec.).

It was found that the measured peak rate value of the reaction falls in the antibody excess region, and hence is acceptable without a post-addition step, if: (1) the foregoing product is less than a threshold value of 88 R.U.$\times$sec. and (2) the elapsed time to the peak rate is less than a threshold value of 50 seconds. That is, if either the product or the elapsed time exceeds the respective threshold value thereof, the post-addition step should be performed to determine the antigen excess or antibody excess condition of the reaction. Moreover, if a peak rate value less than threshold $H_1$ is obtained, the post-addition step should be performed since, as illustrated in FIG. 4 and unlike FIG. 3, values less than $H_1$ could correspond to either an antigen excess or an antibody excess condition. In addition to the foregoing, if the peak rate value exceeds threshold $H_3$, the measurement is rejected as out of range high, and the reaction is repeated at a lower antigen concentration without performing a post-addition step. This latter rejection and remeasurement for values above $H_3$ is thus performed for both IgG (FIG. 3) and IgM (FIG. 4) samples.

With the foregoing criteria, a peak rate value for IgM is acceptable as measured if it falls between threshold values $H_1$ and $H_3$, if the product of the peak rate and elapsed time thereto is less than 88 R.U.$\times$sec., and if the elapsed time to the peak rate is less than fifty seconds. Using the foregoing criteria, it has been found that the post-addition step is unnecessary for as many as seventy percent of a typical population of IgM samples.

In the present method, the second nephelometric signal generated upon post-addition of antigen was differentiated and the peak value of the differentiated signal retained as a measure of the extent of reaction on post-addition. It will be recognized, however, that characteristics of the post-addition nephelometric signal other than the peak rate of signal thereof can be measured to determine the extent of the post-addition reaction. For example, measurement of the overall change in scatter intensity occurring in a fixed time interval after post-addition, as was measured in reference (5) discussed previously, would provide a measure of the extent of the post-addition reaction and hence a determination of the antigen or antibody excess condition of the original reaction.

From the foregoing it will be apparent that the present invention provides an improved method of determining the antigen or antibody excess condition of a reaction which overcomes the delays and other drawbacks of prior methods. Kinetic information, including the peak rate of change of the reaction, is evaluated to determine if post-addition of reactant should be employed for determining the excess condition. Significantly, post-addition is performed only if the measure of antigen concentration is ambiguous. For some reactions, the measurements are determined to be acceptable by the present invention without requiring post-addition. For other reactions, if the measurement is determined to be unacceptable, the reaction is immediately repeated without requiring post-addition. By employing post-addition only for reactions producing ambiguous measurements, it has been possible to eliminate the post-addition operation for up to seventy percent of IgM samples and ninety percent of IgG samples. Moreover, while preferred embodiments of the invention have been illustrated and described, various modifications may be made therein without departing from the spirit and scope of the invention as defined by the appended claims.

What is claimed is:

1. In a method of nephelometric analysis wherein antigen and antibody reaction components are reacting in a first reaction and a rate signal is generated as a time rate of change of a nephelometric signal developed from the first reaction, the peak value of the rate signal providing a measure of a characteristic of one of the reaction components in the first reaction, the improvement comprising the steps of:

establishing a range of peak values for which a measured peak value will provide an ambiguous measure of the characteristic of the one reaction component, a measured peak value within the range of peak values providing an acceptable measure of the characteristic if the first reaction is in antibody excess;

measuring a first peak value of the rate signal while the first reaction is proceeding; and comparing the measured peak value with the range of peak values to determine the existence of an ambiguity in the measured characteristic indicated by the first peak value whereby subsequent addition of a reaction component to the first reaction may be utilized to establish the antigen or antibody excess condition of the first reaction if the comparing step indicates an ambiguity in the measured characteristic.

2. The method of claim 1 wherein the step of establishing a range of peak values includes:

establishing an upper limit for measured peak values above which the first reaction is regarded as being in antigen excess or near-equivalence; and establishing a lower limit for measured peak values below which a measured peak value is unlikely to occur in antigen excess and hence for peak values below which the first reaction is regarded as being in antibody excess.

3. The method of claim 2 comprising the further steps of:

adding reaction component to the first reaction if the comparing step indicates an ambiguity in the measured characteristic to produce a second reaction;

developing a second nephelometric signal from the second reaction; and measuring the second nephelometric signal to determine whether the first reaction is in an antigen or antibody excess condition.

4. The method of claim 3 wherein the step of adding a reaction component to the first reaction is performed during progress of the first reaction after measurement of the first peak value.

5. The method of claim 3 wherein the step of adding a reaction component to the first reaction is performed after the rate signal reaches a predetermined threshold value following measurement of the first peak value.

6. The method of claim 3 wherein the step of measuring the second nephelometric signal includes the steps of:

generating a second rate signal as a time rate of change of the second nephelometric signal;

measuring a peak value of the second rate signal; and comparing the measured peak value of the second rate signal to predetermined criteria therefor to determine the antigen or antibody excess condition.

7. The method of claim 2 including the further step of:

repeating the first reaction at a lower relative concentration of the antigen reaction component if the first measured peak value exceeds the upper limit.

8. The method of claim 2 including the further steps of:

establishing a limit for measured peak values below which background noise and peak values compete; and repeating the first reaction at a higher relative concentration of the antigen reaction component if the first measured peak value is less than this latter limit.

9. In a method of nephelometric analysis wherein antigen and antibody reaction components are reacting in a first reaction and a rate signal is generated as a time rate of change of a nephelometric signal developed from the first reaction, the peak value of the rate signal providing a measure of a characteristic of one of the reaction components in the first reaction, the improvement comprising the steps of:

measuring a first peak value of the rate signal while the first reaction is proceeding;

measuring the elapsed time from the start of the first reaction to the occurrence of the peak value of the rate signal;

multiplying the peak value by the elapsed time thereto;

establishing a first threshold for values of the product of the peak value and elapsed time above which an ambiguity in the measured characteristic is indicated;

establishing a second threshold for values of the elapsed time to the peak value above which an ambiguity in the measured characteristic is indicated even if the product is less than the first threshold; and comparing the product and the elapsed time with the respective first and second threshold values to determine the existence of an ambiguity in the measured characteristic whereby subsequent addition of a reaction component to the first reaction may be utilized to establish the antigen or antibody excess condition of the first reaction if the comparing step indicates an ambiguity in the measured characteristic.

10. The method of claim 9 comprising the further steps of:

adding reaction component to the first reaction if the comparing step indicates an ambiguity in the measured characteristic to produce a second reaction;

developing a second nephelometric signal from the second reaction; and measuring the second nephelometric signal to determine whether the first reaction is in an antigen or antibody excess condition.

11. The method of claim 10 wherein the step of adding reaction component to the first reaction is performed during progress of the first reaction after measurement of the peak value.

12. The method of claim 10 wherein the step of adding reaction component to the first reaction is performed after the rate signal reaches a predetermined threshold value following measurement of the first peak value.

13. The method of claim 10 including the step of measuring the second nephelometric signal includes the steps of:
generating a second rate signal as a time rate of change of the second nephelometric signal;
measuring a peak value of the second rate signal; and
comparing the measured peak value of the second rate signal to predetermined criteria therefor to determine the antigen or antibody excess condition.

14. The method of claim 9 including the further steps of:
establishing a threshold for measured peak values below which an ambiguity in the measured characteristic is indicated; and
comparing the first measured peak value with the latter threshold to determine the existence of an ambiguity in the measured characteristic.

15. The method of claim 9 including the further steps of:
establishing an upper threshold for measured peak values above which the first reaction is regarded as being in antigen excess or near-equivalence; and
repeating the first reaction at a lower relative concentration of the antigen reaction component if the first measured peak value exceeds the upper limit.

16. In a method of nephelometric analysis wherein antigen and antibody reaction components are reacting in a first reaction and a rate signal is generated as a time rate of change of a nephelometric signal developed from the first reaction, the peak value of the rate signal providing a measure of a characteristic of one of the reaction components in the first reaction, the improvement comprising the steps of:
establishing an upper limit for measured peak values above which the first reaction is regarded as being in antigen excess or near-equivalence;
measuring a first peak value of the rate signal while the first reaction is proceeding;
comparing the measured peak value with the upper limit; and
repeating the first reaction at a lower relative concentration of the antigen reaction component if the first measured peak value exceeds the upper limit.

17. The method of claim 12 including the further steps of:
establishing a lower limit for measured peak values below which a measured peak value is unlikely to occur if the first reaction is in antigen excess and hence for measured peak values below which the first reaction is regarded as being in antibody excess;
the upper limit and the lower limit establishing a range of peak values therebetween for which a measured peak value provides an ambiguous measure of the characteristic, a measured peak value within the range providing an acceptable measure of the reaction characteristic if the first reaction is in antibody excess;
comparing the first measured peak value with the range of peak values to determine the existence of any ambiguity in the measured characteristic indicated by the first peak value whereby subsequent addition of a reaction component to the first reaction may be utilized to establish the antigen or antibody excess condition of the first reaction if the comparing step indicates an ambiguity in the measured characteristic.

18. In a method of nephelometric analysis wherein antigen and antibody reaction components are reacting in a first reaction and a rate signal is generated as a time rate of change of a nephelometric signal developed from the first reaction, the peak value of the rate signal providing a measure of a characteristic of one of the reaction components in the first reaction, the improvement comprising the steps of:
establishing a lower limit for measured peak values below which a measured peak value is unlikely to occur if the first reaction is in antigen excess and hence for measured peak values below which the first reaction is regarded as being in antibody excess;
measuring a first peak value of the rate signal while the first reaction is proceeding;
comparing the measured peak value with the lower limit; and
identifying the first reaction as being in antibody excess if the peak value is less than the lower limit.

19. The method of claim 18 including the further steps of:
establishing a signal-to-noise limit for measured peak values above which measured peak values may be discriminated from noise; and
accepting the first peak value as the measure of the characteristic if the peak value is less than the lower limit and greater than the signal-to-noise limit.

* * * * *